United States Patent [19]
Scher et al.

[11] Patent Number: 6,077,522
[45] Date of Patent: Jun. 20, 2000

[54] MICROCAPSULES CONTAINING SUSPENSIONS OF BIOLOGICALLY ACTIVE COMPOUNDS AND ULTRAVIOLET PROTECTANT

[75] Inventors: Herbert B. Scher, Moraga; Jin Ling Chen, El Cerrito, both of Calif.

[73] Assignee: Zeneca Limited, London, United Kingdom

[21] Appl. No.: 09/122,218

[22] Filed: Jul. 23, 1998

Related U.S. Application Data

[60] Division of application No. 08/430,030, Apr. 27, 1995, Pat. No. 5,846,554, which is a continuation-in-part of application No. 08/354,409, Dec. 12, 1994, which is a continuation of application No. 08/153,111, Nov. 15, 1993, abandoned.

[51] Int. Cl.[7] .................................................. A01N 25/08
[52] U.S. Cl. ...................... 424/408; 424/405; 424/406; 424/417; 424/421; 424/490; 424/497
[58] Field of Search ..................... 424/405, 406, 424/408, 409, 417–421, 489–502; 504/116; 428/402.21, 402.24

[56] References Cited

U.S. PATENT DOCUMENTS

| | | | |
|---|---|---|---|
| Re. 29,238 | 5/1977 | Dimitri et al. | 71/101 |
| 2,090,109 | 8/1937 | Coe | 167/24 |
| 2,800,458 | 7/1957 | Green | 252/316 |
| 3,242,051 | 3/1966 | Hiestand et al. | 167/81 |
| 3,541,203 | 11/1970 | Fogle et al. | 424/17 |
| 3,839,561 | 10/1974 | Bordenca | 424/174 |
| 4,056,610 | 11/1977 | Barber et al. | 424/32 |
| 4,094,969 | 6/1978 | Batzer et al. | 424/78 |
| 4,140,516 | 2/1979 | Scher | 71/88 |
| 4,184,866 | 1/1980 | Dellicolli et al. | 71/65 |
| 4,285,720 | 8/1981 | Scher | 71/88 |
| 4,328,203 | 5/1982 | Spence et al. | 424/16 |
| 4,557,755 | 12/1985 | Takahashi et al. | 71/100 |
| 4,722,838 | 2/1988 | Tocker | 424/81 |
| 4,844,896 | 7/1989 | Bohm et al. | 424/89 |
| 4,936,916 | 6/1990 | Shinmitsu et al. | 106/21 |
| 4,938,797 | 7/1990 | Hässlin et al. | 71/118 |
| 4,948,586 | 8/1990 | Bohm et al. | 424/406 |
| 4,956,129 | 9/1990 | Scher et al. | 264/4.7 |
| 5,206,021 | 4/1993 | Dookhith et al. | 424/405 |
| 5,254,344 | 10/1993 | Dookhith et al. | 424/405 |
| 5,418,010 | 5/1995 | Janda et al. | 427/213.31 |
| 5,662,916 | 9/1997 | Nastke et al. | 424/408 |
| 5,679,366 | 10/1997 | Navayanan et al. | 424/409 |
| 5,759,561 | 6/1998 | Angst et al. | 424/407 |

FOREIGN PATENT DOCUMENTS

| | | |
|---|---|---|
| 270742 | 6/1988 | European Pat. Off. . |
| 369614 | 5/1990 | European Pat. Off. . |
| 63/97668 | 4/1988 | Japan . |
| 929402 | 6/1963 | United Kingdom . |
| 2011341 | 7/1979 | United Kingdom . |
| 81/02505 | 9/1981 | WIPO . |
| 83/03521 | 10/1983 | WIPO . |
| 91/12884 | 9/1991 | WIPO . |
| 92/10285 | 6/1992 | WIPO . |
| 92/19102 | 11/1992 | WIPO . |
| 95/13698 | 5/1995 | WIPO . |

OTHER PUBLICATIONS

Derwent Publications Ltd., Dec. 11, 1994, AN 95–059629.
Ignoffo et al., J. Econ. Entomology 64, 850 (1971).
Hypermer dispersant Preliminary Bulletin '86.
Smith et al., *Colloids and Surfaces—A: Physicochemical and Engineering Aspects 88*, p. 67 (1994).
Manufacturing Chemist, Jul. 1994, pp. 14–16.
TIOVEIL brochure '90.
SPECTRAVEIL brochure '89.

*Primary Examiner*—Neil S. Levy
*Attorney, Agent, or Firm*—David P. LeCroy

[57] ABSTRACT

Microcapsules containing a biologically active material which is sensitive to ultraviolet light are prepared which contain an ultraviolet light protectant selected from titanium dioxide, zinc oxide and mixtures thereof, suspended and thoroughly dispersed in a liquid.

20 Claims, 1 Drawing Sheet

MICROCAPSULES CONTAINING SUSPENSIONS OF BIOLOGICALLY ACTIVE COMPOUNDS AND ULTRAVIOLET PROTECTANT

This application is a divisional application of Ser. No. 08/430,030, now U.S. Pat. No. 5,846,554 filed on Apr. 27, 1995, and issued on Dec. 8, 1998, which is a continuation-in-part of application Ser. No. 08/354,409, filed on Dec. 12, 1994, which is a continuation of application Ser. No. 08/153,111, filed on Nov. 15, 1993 and abandoned.

BACKGROUND AND PRIOR ART

This invention pertains to an improvement in the invention described in application Ser. No. 08/354,409, filed Dec. 24, 1994, and in particular in producing microcapsules containing biologically active compounds and further containing a suspended ultraviolet protectant agent.

As pointed out in application Ser. No. 08/354,409, while various types of microencapsulation techniques have been used to prepare microcapsules of biologically active compounds for pesticidal use, no satisfactory techniques to produce a microcapsule containing a solid biologically active pesticide suspended in a liquid had previously been known. There were several reasons for this, particularly the following difficulties:

1. It is necessary to produce a stable suspension of the biologically active solid in a water-immiscible liquid. If dispersants or surfactants are used, they must not interfere with further processes of dispersion used in making the microcapsules.

2. The suspension of the solid must be dispersed in water to produce stable well-dispersed droplets, preferably very small droplets of an organic-phase suspension dispersed in water. This requires high shear forces which would tend to break down the droplets and/or release the solid from suspension.

3. The presence of one or more surfactants can make the dispersed droplet system unstable and produce phase inversion.

4. The suspended solid is liable to migrate to the aqueous phase, particularly when emulsifying surfactants are used.

Application 08/354,409 describes techniques for producing microencapsulated formulations of a solid biologically active compound suspended in a liquid. The product is produced by essentially a three-step process. In the first step, the solid biologically active material is produced with a required particle size, for example by a milling process. In the second step, the solid biologically active compound is suspended in an organic liquid, preferably one which is a poor solvent for the solid and which is immiscible with water. The liquid, however, must be polar enough to dissolve the prepolymers used in the microencapsulation process. Alternatively, the solid may be first suspended in a liquid and then milled. In the third step, a physical dispersion of this water immiscible phase in an aqueous phase is prepared.

Some biologically active materials are adversely affected by ultraviolet or actinic light; even when they are microencapsulated, the active material in the capsule may still become degraded in the presence of light. A number of techniques have been proposed to provide ultraviolet light protection to microencapsulated materials. For example, Ignoffo et al., J. Economic Entomology, 64, 850 (1971) discloses use of cellulose, carbon, aluminum powder and aluminum oxide in protecting encapsulated virus samples from ultraviolet radiation. The authors do not describe the process by which the microcapsules were prepared. U.S. Pat. No. 3,541,203 describes the use of carbon black and other ultraviolet absorbers such as metal flakes, metal oxide particles, metal sulfides and other commonly used pigments to provide ultraviolet protection to a virus contained within a polymeric matrix. U.S. Pat. Nos. 4,844,896 and 4,948,586 disclose the use of a number of organic dyes and other sunscreening agents such as benzophenone, PABA and benzil (or mixtures thereof) for protection of encapsulated viruses. U.S. Pat. No. 4,328,203 discloses production of a microencapsulated pathogenic viral, bacterial or fungal material in a coacervate microbead comprised of a nucleic acid and a proteinaceous material, in which the microbead structure itself is a UV protectant. Finally, PCT application WO92/19102 discloses another type of microcapsule in which the encapsulating agent itself, this time lignin, also serves as the sunscreen.

SUMMARY OF THE INVENTION

This invention comprises microcapsules and a process for their preparation, and in particular comprises [1] a microcapsule containing a liquid comprising an ultraviolet light sensitive, biologically active compound and an effective amount of a particulate ultraviolet light protectant selected from titanium dioxide, zinc oxide and mixtures thereof suspended and thoroughly dispersed in the liquid; and [2] a process for preparing microcapsules containing an ultraviolet light sensitive biologically active compound which comprises a liquid and an effective amount of a particulate ultraviolet light protectant selected from titanium dioxide, zinc oxide and mixtures thereof suspended and thoroughly dispersed in the liquid, comprising the steps of: (a) preparing a suspension of the ultraviolet light protectant having average particle size of about 0.01–2 microns in an organic liquid which is immiscible with water and which contains an ultraviolet light sensitive biologically active material, in which the protectant is thoroughly dispersed in the liquid; (b) introducing the suspension of step (a) into water containing a protective colloid and optionally a surfactant capable of maintaining the organic liquid as droplets in the water without extracting solids from the organic liquid into the water, the organic liquid containing in solution one or more prepolymers which can react to form a polymer at the interface of the organic liquid and water; (c) mixing the suspension of organic liquid in the aqueous phase under high shear to form an oil-in-water emulsion; and (d) adjusting, if necessary, the temperature and/or pH of the oil-in-water emulsion such that a polymerization reaction takes place at the organic liquid/water interface to form the microcapsules.

DETAILED DESCRIPTION OF THE INVENTION

Figure 1:
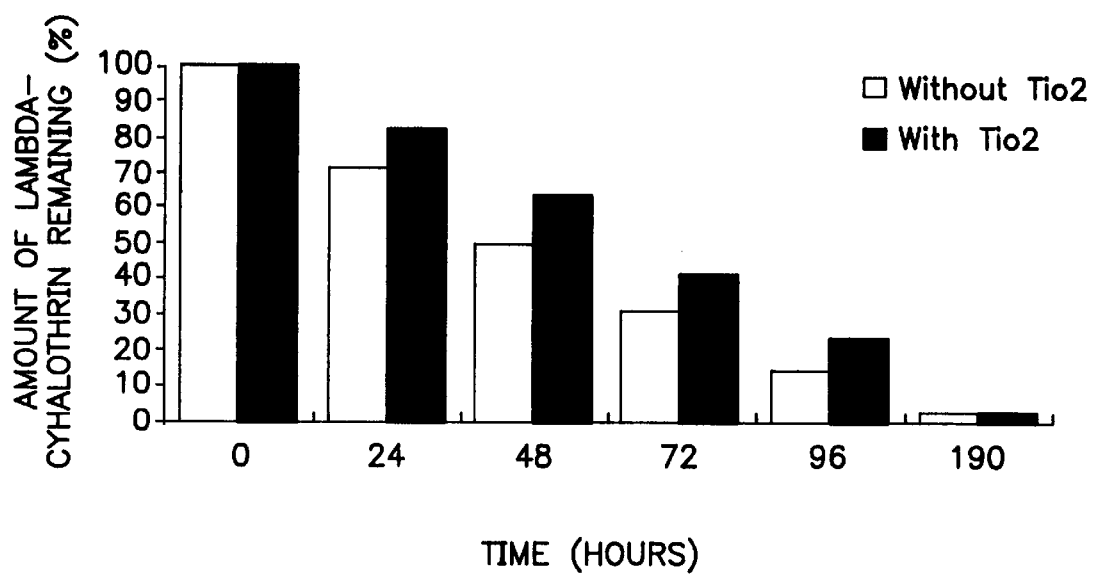

In general, the invention uses the process described in the parent application hereof, Ser. No. 08/354,409, filed Dec. 24, 1994, to produce microcapsules. This technique will be described herein. In the parent application, the technique was utilized for producing microcapsules containing a suspension of a biologically active solid in a liquid. In the present invention, the technique is utilized for preparing a suspension of a solid ultraviolet light protectant material in a liquid which comprises biologically active material. By "comprises", it is meant that the biologically active material may also be in the form of a solid suspended in the liquid, or may be dissolved in the liquid, or may itself constitute the liquid in which the ultraviolet light protectant is suspended.

In another embodiment, the microcapsule may contain a suspension of a solid biologically active compound in a liquid which comprises a second biologically active compound (for example, the second biologically active compound is the liquid or is dissolved in the liquid), and which also contains a thoroughly dispersed particulate ultraviolet light protectant.

The biologically active material which is to be protected in this invention may be any of those known to be subject to degradation or decomposition by ultraviolet light. Notable among such compounds are the pyrethroids and pyrethrins. Many of the pyrethroids are known to be susceptible to degradation by ultraviolet light including permethrin, cypermethrin, deltamethrin, fenvalerate, cyfluthrin, resmethrin, allethrin, etofenprox, and lambda-cyhalothrin. Other biologically active materials which are known to be susceptible to degradation or decomposition by ultraviolet light include the herbicides trifluralin, ioxynil and napropamide, the insecticides pirimiphos-methyl and chlorpyrifos and the fungicide azoxystrobin. Microcapsules of this invention may contain two or more ultraviolet light sensitive biologically active materials.

The liquid utilized in this invention may be a liquid biologically active material which itself is susceptible to degradation by ultraviolet light, or a biologically active material which is not normally so susceptible (but in which there is suspended a second biologically active material which is light-sensitive), or an organic solvent which is immiscible in water and in which the ultraviolet light sensitive material is suspended or dissolved. The liquid, in any case, should be sufficiently polar to dissolve the prepolymer or prepolymers used to form the microcapsule wall.

For solvents, suitable examples are (depending on the types of microcapsule) aromatic hydrocarbons such as xylenes or naphthalenes, aliphatic solvents such as aliphatic or cycloaliphatic hydrocarbons, e.g., hexane, heptane and cyclohexane, alkyl esters including alkyl acetates and alkyl phthalates, ketones such as cyclohexanone or acetophenone, chlorinated hydrocarbons, and vegetable oils. The solvent may be a mixture of two or more of the above solvents.

The preferred materials for the microcapsule wall may be any of those commonly used. Two examples are a polyurea, formed as described in U.S. Pat. No. 4,285,720. or a urea-formaldehyde polymer as described in U.S. Pat. No. 4,956,129.

The ultraviolet light protectant used in this invention is titanium dioxide. zinc oxide, or a mixture of titanium dioxide and zinc oxide. In general, the ultraviolet light protectant is used in an amount of from about 0.1 to about 50 weight %, preferably from about 1 to about 10 weight %, with respect to the organic phase. Mixtures of titanium dioxide and zinc oxide will contain these two substances in a weight ratio of from about 1:10 to about 10:1.

The process comprises the following steps:

Step 1. Obtaining the ultraviolet light protectant with a preferred particle size. The protectant may be commercially available in the desired particle size. If not, it is treated suitably by a milling process. The preferred average particle size of this protectant is about 0.01–2 microns, preferably about 0.02–0.5 microns. If the microcapsules are to contain a solid biologically active material suspended in the liquid, that material should have an average particle size of from about 0.01 to about 50, preferably from about 1 to about 10, microns.

Step 2. Suspending the ultraviolet light protectant in an organic liquid. The liquid must be immiscible with water, but polar enough to dissolve the prepolymers used in the microencapsulation process. The ultraviolet light protectant must also be thoroughly dispersed in the liquid; i.e., dispersed into individual particles that are not agglomerated.

The dispersion is preferably carried out by means of a dispersant which is capable of keeping the protectant solid in the liquid but which does not allow the solid to be extracted into the water when the suspension is dispersed into water. In addition, when the suspension is added to water, the dispersant must not allow phase inversion to occur, i.e., the water must not be allowed to be taken into the organic liquid to form a water-in-oil emulsion.

The exact choice of dispersants will depend on the nature of the ultraviolet light protectant and the type of organic liquid. Preferred dispersants are certain nonionic surfactants which act by steric hindrance and are active only at the protectant solid/organic liquid interface and do not act as emulsifying agents. Such dispersants are suitably made up of (a) a polymeric chain having a strong affinity for the liquid and (b) a group which will absorb strongly to the solid. Examples of such dispersants are those of the Hypermer and Atlox lines, available from the ICI group of companies. including Hypermer PS1, Hypermer PS2, Hypermer PS3, Atlox LP1, Atlox LP2, Atlox LP4, Atlox LP5, Atlox LP6, and Atlox 4912; and Agrimer polymers such as Agrimer AL-216 and AL-220, available from GAF.

In general, the range of dispersant concentration used is from about 0.01 to about 10 percent by weight based on the organic phase, but higher concentrations of dispersant may also be used.

If the microcapsules also contain a suspended solid biologically active material, the same considerations apply with respect to suspending and dispersing it as are mentioned above for the ultraviolet light protectant.

Alternatively, the procedures of these steps 1 and 2 above may be varied by first suspending and dispersing the ultraviolet light protectant in the organic liquid, with the protectant having a particle size larger than that mentioned above, and then conducting a milling process (media milling) to reduce the particle size of the protectant to that mentioned above.

In any event, no matter exactly how it is accomplished, the ultraviolet light protectant must be thoroughly dispersed in the organic phase.

Step 3: A physical dispersion of a water-immiscible phase in an aqueous phase is prepared. To obtain the appropriate dispersion, the organic phase is added to the aqueous phase, with stirring. A suitable dispersing means is employed to disperse the organic phase in the liquid phase. The means may be any high shear device, so as to obtain a desired average droplet (and corresponding microcapsule particle) size within the range of from about 1 to about 200 microns. Preferably the average droplet size is from about 1 to about 30 microns, most preferably from about 2 to about 20 microns. Once the proper droplet size is obtained, the dispersion means is discontinued. Only mild agitation is required for the remainder of the process. The water-immiscible (organic liquid) phase comprises the solid ultraviolet light protectant and optionally also a solid biologically active material suspended in the liquid to be encapsulated, prepared as described above in Steps 1 and 2. The aqueous phase is comprised of water and a material termed a "protective colloid". Preferably it further contains a surfactant.

In general, the surfactant or surfactants in the aqueous phase may be anionic or non-ionic surfactants with an HLB range of from about 12 to about 16 that is high enough to form a stable oil-in-water emulsion. If more than one surfactant is used, the individual surfactants may have values lower than 12 or higher than 16 as long as the overall HLB value of the surfactants when combined will be in the range of 12–16. Suitable surfactants include polyethylene glycol ethers of linear alcohols, ethoxylated nonylphenols, naphthalene sulfonates, salts of long chain alkylbenzene sulfonates, block copolymers of propylene oxide and ethylene oxide and anionic/nonionic blends. Preferably the hydrophobic portion of the surfactant has chemical characteristics similar to the organic liquid. Thus, when the organic liquid is an aromatic solvent, the surfactant would suitably be an ethoxylated nonylphenol.

Especially preferred surfactants are Tergitol NP7, Tergitol XD, Tergitol NP40 and Tergitol 15-S-20, available from Union Carbide and Witconate 90, available from Witco.

In general, the range of surfactant concentration in the process is from about 0.01 to about 10.0 percent by weight, based on the aqueous phase, but higher concentrations of surfactant may also be used.

The protective colloid present in the aqueous (continuous) phase must absorb strongly onto the surface of the oil droplets. Suitable colloid-forming materials include one or more of polyacrylates, methyl cellulose, polyvinyl alcohol, polyacrylamide, poly(methylvinyl ether/maleic anhydride), graft copolymers of polyvinyl alcohol and methylvinyl ether/maleic acid (hydrolyzed methylvinyl ether/maleic anhydride, see U.S. Pat. No. 4,448,929. which is hereby incorporated by reference herein), and alkali metal or alkaline earth metal lignosulfonates. Preferably, however, the protective colloid is selected from alkali metal and alkaline earth metal lignosulfonates, most preferably sodium lignosulfonates.

There must be sufficient colloid present to afford complete coverage of the surfaces of all the droplets of the organic liquid. The amount of protective colloid employed will depend on various factors, such as molecular weight, compatibility, etc. The protective colloid can be added to the aqueous phase prior to the addition of the organic phase, or can be added to the overall system after the addition of the organic phase or the dispersion of it. The protective colloid is generally present in the aqueous phase in an amount of from about 0.1 to about 10.0 percent by weight.

Any surfactant used in the aqueous phase must not displace the protective colloid from the surface of the droplets of organic liquid.

The preferred average particle size of the droplets of the water-immiscible liquid containing a biologically active solid is 1–200 microns, preferably 1–30 microns and more preferably 2–20 microns. Particle size can be adjusted according to the end use of the microcapsules by adjusting stirring speed and time, and by the choice of surfactants and the amount of surfactants employed.

In order to obtain the microcapsules. the organic liquid and/or the water must contain one or more materials which can react to form a polymer at the interface between the organic liquid and the water.

In the process described in U.S. Pat. No. 4,285,720, polyisocyanates are dissolved in the organic phase (i.e., at Step 2 in the above procedure) and polymerization takes place by hydrolysis of the prepolymers at the water/organic liquid interface to form amines which, in turn, react with unhydrolyzed monomers to form the polyurea microcapsule wall. A single compound or a mixture of two or more polyisocyanates may be used. Of the polyisocyanates, polymethylene polyphenylisocyanate and isomeric mixtures of toluene diisocyanate are preferred. Particularly preferred are mixtures of polymethylene polyphenylisocyanate with isomeric mixtures of toluene diisocyanate.

The amount of the organic polyisocyanate used in the process will determine the wall content of the microcapsules formed. In general, the polyisocyanate (or microcapsule wall formed from it) content will comprise from about 2.0 to about 75.0 percent by weight of the microcapsule. Most preferably the wall will comprise from about 4 to about 15% by weight of the microcapsule.

The dispersion is maintained in a temperature range of from about 20° C. to about 90° C., preferably from about 40° to about 60° C., during which the condensation reaction takes place to form the polyurea at the interfaces between the droplets of the organic phase and the aqueous phase.

Another suitable system for forming microcapsules is described in U.S. 4,956,129, in which the polymer is formed from an etherified urea-formaldehyde prepolymer in which 50–98% of the methylol groups have been etherified with a $C_4$–$C_{10}$ alcohol. The prepolymer is added to the organic phase. Self-condensation of the prepolymer takes place under the action of heat at low pH.

To form the microcapsules, the temperature of the two-phase mixture is raised to a value of from about 20° C. to about 90° C., preferably from about 40° C. to about 90° C., most preferably from about 40° C to about 60° C. Depending on the system, the pH value may be adjusted to an appropriate level. For the purpose of this invention a pH of 2 is appropriate.

The following are examples of preparations of compositions of this invention. Ingredients used in the following examples were:

lambda-cyhalothrin, technical grade (88% purity)

Solvesso 200 aromatic solvent (available from Exxon)

titanium dioxide—Examples 1 and 2: USP328—0.3 micron particle size, from Whittaker, Clark & Daniels Ltd.; Example 3: Tiosorb UFO2, 0.02 micron size, from Tioxide Specialties Ltd.

Hypermer LP1, Hypermer LP5 and Atlox 4912 dispersants (available from ICI)

Reax 100M protective colloid (sodium salt of lignosulfonic acid, 40% wt. solution in water, available from Westvaco Chemicals Kelzan (xanthan gum, available from Monsanto)

Proxel GXL (biocide, available from ICI) The amounts of the ingredients are given in the examples.

GENERAL PROCEDURE

A solution of lambda-cyhalothrin in Solvesso 200 solvent was prepared. The dispersants were added, followed by the titanium dioxide, and the resulting suspension agitated with a high shear stirrer. After the titanium dioxide was well dispersed, polymethylene polyphenylisocyanate and toluene diisocyanate were added to complete the organic phase.

This phase was introduced to the aqueous phase with agitation with a high shear stirrer to form an oil-in-water emulsion. The average droplet size was 3.0±1 microns (Examples 1 and 2) and about 12 microns (Example 3). The temperature was then raised to 50° C. over a 30-minute period while maintaining mild agitation, and then maintained at 50° C. for 3 hours. The resulting suspension of microcapsules was allowed to cool to room temperature. In Examples 1 and 2 the additional ingredients were added (to improve the properties of the aqueous suspension of microcapsules) and the pH was adjusted to 5.0 with sulfuric acid.

EXAMPLE 1

| Component | Composition Weight, g | Weight, % |
|---|---|---|
| ORGANIC PHASE | | |
| Lambda-cyhalothrin | 113.2 | 28.3 |
| Solvesso 200 | 58.4 | 14.6 |
| Titanium dioxide | 9.7 | 2.4 |
| Hypermer LP5 | 6.1 | 1.5 |
| Hypermer LP1 | 2.1 | 0.5 |
| Isocyanates | 15.3 | 3.8 |
| AQUEOUS PHASE | | |
| Reax 100M | 10.5 | 2.6 |
| Witconate 90 | 1.0 | 0.3 |
| Tergitol XD | 3.1 | 0.8 |
| Water | 176.5 | 44.2 |
| ADDITIONAL INGREDIENTS | | |
| Ammonia (30% wt aqueous solution) | 2.0 | 0.5 |
| Kelzan | 0.5 | 0.1 |
| Proxel GXL | 0.4 | 0.1 |
| Concentrated Sulfuric Acid | 1.2 | 0.3 |
| TOTAL | 400.0 | 100.0 |

EXAMPLE 2

| Component | Composition Weight, g | Weight, % |
|---|---|---|
| ORGANIC PHASE | | |
| Lambda-cyhalothrin | 113.2 | 28.3 |
| Solvesso 200 | 58.4 | 14.6 |
| Titanium dioxide | 9.7 | 2.4 |
| Atlox 4912 | 8.2 | 2.0 |
| Isocyanates | 15.3 | 3.8 |
| AQUEOUS PHASE | | |
| Reax 100M | 10.5 | 2.6 |
| Witconate 90 | 1.0 | 0.3 |
| Tergitol XD | 3.1 | 0.8 |
| Water | 176.5 | 44.2 |
| ADDITIONAL INGREDIENTS | | |
| Ammonia (30% wt aqueous solution) | 2.0 | 0.5 |
| Kelzan | 0.5 | 0.1 |
| Proxel GXL | 0.4 | 0.1 |
| Concentrated Sulfuric Acid | 1.2 | 0.3 |
| TOTAL | 400.0 | 100.0 |

EXAMPLE 3

| Component | Composition Weight, g | Weight, % |
|---|---|---|
| ORGANIC PHASE | | |
| Napropamide (technical grade) | 52.0 | 13.0 |
| Solvesso 200 | 94.1 | 23.5 |
| Titanium dioxide | 31.5 | 7.9 |
| Hypermer LP6 | 8.4 | 2.0 |
| Isocyanates | 14.7 | 3.7 |
| AQUEOUS PHASE | | |
| Reax 100M | 14.7 | 3.7 |
| Tergitol 15-s-7 (20% wt aqueous solution) | 12.6 | 3.2 |
| Gelvatol 40/10 (20% wt aqueous solution) | 9.5 | 2.4 |
| Water | 162.5 | 40.6 |
| TOTAL | 400.0 | 100.0 |

DETERMINATION OF PROTECTIVE EFFECT

Glass Slide Evaluation

A sample of microcapsules containing titanium dioxide prepared as in Example 1 (according to the invention; indicated in Table 1 as Example 1b) was spread on a glass slide and exposed to a xenon lamp (simulating sunlight) for up to three days. Comparative tests were conducted with identical amounts of microcapsules similarly prepared, but differing from that of the invention as indicated below in containing a different ultraviolet light protectant (Example 1a), similarly containing titanium dioxide but lacking a dispersant (Example 1c), prepared utilizing titanium dioxide in the aqueous phase only (Example 1d) or lacking an ultraviolet light protectant (Example 1e). The microcapsules were analyzed to determine the amount of lambda-cyhalothrin present in the formulations at the initiation of exposure to ultraviolet light and the amount present after one and three days' exposure.

As can be seen from the results in the following Table 1, microcapsules produced according to this invention (Example 1b) provided the best protection against degradation of lambda-cyhalothrin by ultraviolet light. After one day's exposure, most of the lambda-cyhalothrin was still present, whereas with the comparative microcapsules the amount of lambda-cyhalothrin remaining ranged from approximately one-fourth to nearly one-sixth of the original amount. Even after three days' exposure, microcapsules of this invention still contained nearly one-half of the lambda-cyhalothrin originally present.

TABLE 1

| EXAMPLE | UV PROTECTANT TYPE | WT. % IN FORMULATION | % LAMBDA-CYHALOTHRIN REMAINING AFTER IRRADIATION | | |
|---|---|---|---|---|---|
| | | | 0 DAYS | 1 DAY | 3 DAYS |
| 1a | Waxoline black + Hypermer dispersants | 2.5 | 100 | 17.9 | |
| 1b | Titanium dioxide + Hypermer dispersants | 2.5 | 100 | 82.1 | 47.9 |
| 1c | Titanium dioxide without dispersants | 2.5 | 100 | 20.8 | |

TABLE 1-continued

| EXAMPLE | UV PROTECTANT | | % LAMBDA-CYHALOTHRIN REMAINING AFTER IRRADIATION | | |
|---|---|---|---|---|---|
| | TYPE | WT. % IN FORMULATION | 0 DAYS | 1 DAY | 3 DAYS |
| 1d | Titanium dioxide outside capsule - in aqueous phase only | 2.5 | 100 | | 17.9 |
| 1e | None | — | 100 | | 24.2 |

Foliar Persistence on Cotton

A sample of the material designated above as Example 1b was tested in comparison with microcapsules similarly prepared containing the same amount of lambda-cyhalothrin but having no titanium dioxide and no dispersants.

All samples of microcapsules were diluted with water and sprayed on cotton plants at an application rate of 50 g lambda-cyhalothrin/hectare.

Leaf samples from the cotton were taken and processed as follows, with two replicates for each treatment, each time, being taken.

Each replicate involved excising three well exposed leaves, placing them in a glass jar, adding 500 ml acetone, closing the jars and shaking well for 30–45 seconds. The leaves were then carefully but quickly removed, flattened while still drying, sandwiched between sheets of transparent plastic, and photocopied. The leaves were disposed of and their size was measured from the photocopies using an image analyzer.

Then, 2 ml of the mobile phase was added to the samples, the contents of the jar were shaken vigorously and then filtered and analyzed by reverse phase high pressure liquid chromatography.

Samples were taken at 24, 48, 72, 96, and 190 hours after application. FIG. 1 shows, in graphical form, a comparison of the retention of lambda-cyhalothrin in the two formulations tested—one according to the invention, the other identical but without the titanium dioxide and dispersants, and demonstrates the protection of lambda-cyhalothrin in the product of this invention as compared to capsules lacking the protectant.

What is claimed is:

1. A microcapsule containing an organic liquid, a particulate ultraviolet light protectant selected from titanium dioxide, zinc oxide and mixtures thereof suspended and thoroughly dispersed in the organic liquid, and a dispersant which serves to disperse the ultraviolet light protectant in the organic liquid, and to keep it in said liquid, but which does not allow it to be extracted into water.

2. A microcapsule according to claim 1 in which the dispersant is active only at the particulate solid/organic liquid interface and does not act as an emulsifying agent.

3. A microcapsule according to claim 1 in which the dispersant is a nonionic surfactant.

4. A microcapsule according to claim 1 in which the dispersant molecule comprises a polymeric chain having an affinity for the organic liquid and a group which absorbs to the particulate solid.

5. A microcapsule according to claim 1 in which the dispersant is present in an amount of from about 0.01 to about 10 weight percent based on the total weight of the microcapsule and its contents.

6. A microcapsule according to claim 1 in which the particle size of the ultraviolet light protectant is from about 0.01 to about 2 microns.

7. A microcapsule according to claim 1 in which the particle size of the ultraviolet light protectant is from about 0.02 to about 0.5 microns.

8. A microcapsule according to claim 1 in which the ultraviolet light protectant is titanium dioxide.

9. A microcapsule according to claim 1 in which the ultraviolet light protectant is a mixture of titanium dioxide and zinc oxide.

10. A microcapsule according to claim 1 in which the capsule walls are comprised of polyurea.

11. A microcapsule according to claim 1 in which the capsule walls are comprised of a urea-formaldehyde polymer.

12. A microcapsule according to claim 1 further containing an ultraviolet light sensitive, biologically active material.

13. A microcapsule according to claim 12 in which the biologically active material is dissolved in or comprises the organic liquid.

14. A microcapsule according to claim 12 in which the biologically active material is suspended in the liquid.

15. A microcapsule according to claim 12 in which the biologically active material is selected from herbicides, insecticides and fungicides.

16. A microcapsule according to claim 15 in which the biologically active material comprises a fungicide.

17. A microcapsule according to claim 15 in which the biologically active material comprises a herbicide.

18. A microcapsule according to claim 15 in which the biologically active material comprises an insecticide.

19. A microcapsule according to claim 18 in which the biologically active compound comprises a pyrethroid insecticide.

20. A microcapsule according to claim 19 in which the biologically active compound comprises lambda-cyhalothrin.

* * * * *